United States Patent [19]

Noguchi et al.

[11] Patent Number: 4,843,021
[45] Date of Patent: Jun. 27, 1989

[54] IMMUNOLOGICAL ASSAY METHOD

[75] Inventors: Yasuhiko Noguchi, Machida; Masahiro Naito, Kanagawa; Kenji Morinaga, Machida; Yohji Takahashi, Sagamihara; Katsuo Mitani, Fujisawa, all of Japan

[73] Assignees: Shino-Test Laboratory Inc., Kanagawa; Tokuyama Soda Co. Ltd., Yamaguchi, both of Japan

[21] Appl. No.: 79,318

[22] Filed: Jul. 30, 1987

[30] Foreign Application Priority Data

Jul. 30, 1986 [JP] Japan .............................. 61-177651

[51] Int. Cl.⁴ .......................................... G01N 33/546
[52] U.S. Cl. .................................... 436/533; 436/517; 436/534; 436/805
[58] Field of Search ................ 436/517, 533, 534, 805

[56] References Cited

U.S. PATENT DOCUMENTS 4,157,871  6/1979  Anderson et al. .
4,224,304  9/1980  Sawai .............................. 436/534 X
4,268,171  5/1981  Sternberg ....................... 436/805 X

OTHER PUBLICATIONS

Short Communication/Kurzmitteilung, J. Clin. Chem. Clin. Biochem./vol. 23, 1985/No. 11, pp. 787-789.
An Automated Turbidimetric Rate Method for Immunoglobulin Assays, Clinica Chimica Acta, 88 (1978), pp. 523-530.

Primary Examiner—Robert J. Hill, Jr.
Attorney, Agent, or Firm—Browdy and Neimark

[57] ABSTRACT

An immunological assay method, wherein the concentration of a substance to be assayed is calculated from a calibration curve, which is formed in the preparation of a reagent or in the assay of a sample based on parameter(s) determined in the preparation of the reagent, without the need of forming any additional calibration curve each time, is disclosed. By the immunological assay method of the present invention, the concentration of the substance to be assayed can be efficiently and discontinuously determined, when compared with conventional ones. The method of the present invention is particularly suitable for quantitatively determining an antigen or an antibody.

2 Claims, 1 Drawing Sheet

FIG. 1

IMMUNOLOGICAL ASSAY METHOD

BACKGROUND OF THE INVENTION

1. Field of Industrial Application

This invention relates to an immunological assay method. More particularly, it relates to an immunological assay method suitable for quantitatively determining an antigen or an antibody.

2. Prior Art

Known methods for assaying bodily fluid components such as IgG, IgA, Igm, complements C3 and C4 and CRP include nephelometry with the use of an autoanalyzer provided with a built-in computer, latex nephelometry and laser light scattering nephelometry.

Each of these methods comprises reading a change in optical properties caused by an antigen/antibody reaction in a solution in terms of a change in transmitted or scattered light and comparing the obtained data with a calibration curve, which has been formed each time by assaying a standard material of a known concentration, to thereby determine the concentration of the substance to be assayed.

Now operations of the conventional nephelometry with the use of an autoanalyzer will be described in detail.

1. A reagent to be assayed, i.e., a sample is introduced into a container such as a cuvette and incubated in an autoanalyzer at an appropriate temperature, for example, 37° C.
2. A calibration curve is formed with the use of a standard material.
   2-1. A specific equation, for example, $Y = Ax + B/x$ inputted in a built-in ROM or microcomputer in the analyzer according to the item to be assayed is called.
   2-2. The parameters A and B in the above equation are determined depending on the assay of the standard material.
   2-3. A calibration curve is formed by substituting the parameters A and B as defined above in the above equation.
3. The sample is measured and the concentration of the antigen or antibody therein is determined according to the above calibration curve.

When a number of samples are to be assayed, 400 to 500 samples are continuously assayed in a day in general. In the conventional method as described above, it is required to form a new calibration curve each time prior to the initiation of the assay when a series of continuous assays have been completed and the operations are to be carried out again on the next day to approximately one week thereafter.

Thus these operations should be shared between a reagent manufacturer and a user in the following manner.

Reagent manufacturer:
1. Preparing a reagent.
2. Forming a calibration curve with the use of, for example, a graph and determining an equation corresponding to the calibration curve, for example, $Y = Ax + B/x$, which should be informed to a user.

User:
3. Prior to the assay of a sample, assaying a standard material of a known concentration. Based on the results thus obtained, determining the parameters in the above equation and forming a calibration curve therefrom.
4. Effecting a series of continuous assays depending on the calibration curve as formed above.
5. Repeating the procedures of steps 3 and 4 each time assays are newly initiated.

In these conventional methods, which are called calibration systems, it is troublesome to form a calibration curve each time when a few samples are to be assayed or samples should be emergently assayed. Further it is difficult to efficiently utilize a reagent in these cases, since a calibration curve should be formed prior to each assay with the use of a standard material.

SUMMARY OF THE INVENTION

Under these circumstances, the present invention provides an immunological assay method wherein the concentration of a substance in samples to be assayed is calculated from a calibration curve, which is formed in the preparation of a reagent or in the assay of the sample based on parameter(s) determined in the preparation of the reagent, without forming any additional calibration curve each time.

The present invention aims at providing an immunological assay method for efficiently and discontinuously determining the concentrations of a substance to be assayed in various samples.

The present invention further provides a novel system for an immunological assay method.

Further objects of the present invention will be apparent from the following description.

DETAILED DESCRIPTION OF THE INVENTION

It is the greatest feature of the present invention that an immunological assay method, wherein the concentrations of a substance to be assayed in samples are repeatedly determined depending on a calibration curve based on a signal for a decrease in transmitted light or an increase in scattered light, which is caused by a change in the turbidity accompanying the formation of an antigen-antibody complex by an antigen-antibody reaction, determined after a definite time or the maximum velocity or the maximum acceleration thereof, comprises calculating the concentration of said substance to be assayed depending on said calibration curve, which is formed in the preparation of a reagent or in the assay of the samples based on parameter(s) determined in the preparation of the reagent, without the need of forming any additional calibration curve with the use of a standard material of a known concentration prior to each assay, so long as said assays are discontinuously carried out within the term of validity of said reagent.

Comparing with the operations of the conventional immunological assay method with the use of an autoanalyzer as described above, those of the immunological assay method of the present invention will be described now.

1. A sample to be assayed is introduced into a container such as a cuvette and incubated in an autoanalyzer at an appropriate temperature, for example, 37° C.
2. A calibration curve is formed.
   2-1. A specific equation, for example, $Y = Ax + B/x$ inputted in a built-in ROM or microcomputer in the analyzer according to the item to be assayed is called.

2-2. A calibration curve is formed by inputting parameters, e.g., A and B, which are recorded in a magnetic medium attached to the reagent kit.
3. A sample is assayed to thereby determine the concentration of an antigen or an antibody.

In the method of the present invention as described above, parameters of a reagent of the same lot are the same with each other. Therefore the concentrations of the substance to be assayed may be discontinuously and repeatedly determined depending on only the above calibration curve formed in the preparation of the reagents without the need of forming any additional calibration curve with the use of a standard material of a known concentration prior to each assay, as required in a conventional method, so long as a reagent in the same lot is utilized within the term of validity thereof. It is not always necessary to form the calibration curve as mentioned above in the preparation of the reagent. Thus it is also possible to determine said parameters in the preparation of the reagent and to form the calibration curve prior to assaying a sample.

These operations may be shared between a reagent manufacturer and a user in the following manner.

Reagent manufacturer:
1. Preparing a reagent.
2. Forming a calibration curve with the use of a standard material of a known concentration. Namely, forming an equation corresponding to the item to be assayed, for example, $Y=Ax+B/x$, and inputting the same to a computer. Alternately determining parameters corresponding to the reagent, for example, A and B.
3. Recording the information concerning the calibration curve thus formed or the parameters thus determined in a recording medium selected from among:
   i. cards such as magnetic IC and punched cards;
   ii. tapes such as magnetic and cassette tapes;
   iii. floppy disks; and
   iv. graph papers.
   When a graph paper is to be used as a recording medium, the above equation is not inputted to the computer.

User:
1. When no calibration curve has been formed by the manufacturer in the preparation of the reagent, inputting the preliminarily determined parameters to thereby give a calibration curve corresponding to the reagent.
2. Discontinuously assaying samples to thereby determine the concentrations of the substance to be assayed according to the calibration curve as formed above, without forming any additional one prior to each assay.

This method, which is called a noncalibration system, will be described in detail hereinbelow. The calibration curve to be formed in the preparation of a reagent is obtained from straight line(s) and/or curve(s) and expresses the relationship between the concentration, which is already known, of a sample and the turbidity and/or an increase therein, which is caused by reacting the sample whose concentration is known as described above with an assay reagent comprising an antiserum for the sample, salts and polyethylene glycol or a latex sensitized with an antibody or an antigen for the sample, in terms of a decrease in transmitted light or an increase in scattered light accompanying an antigen/antibody reaction in a solution. It is the most usual to form this calibration curve in the preparation of said reagent. However it is also possible to determine only equation(s) for the straight line(s) and/or curve(s) and to separately prepare the parameter(s) corresponding to the coefficient(s) in the straight line(s) and/or curve(s). Then the calibration curve may be formed from these parameter(s) in assaying a sample. When this calibration curve has been preliminarily recorded on a graph paper, routine assays of samples may be discontinuously carried out by using the same, without requiring any standard material of a known concentration each time. Alternately, the above calibration curve may be recorded in a recording medium selected from among cards such as IC and magnetic cards, floppy disks and tapes such as cassetts and magnetic tapes, as described above. It is also possible in this case to calculate the concentration of a sample without using any standard material of a known concentration. It may be generally determined depending on the capacity of a recording medium whether the information is recorded in the medium in the form of a calibration curve itself or parameter(s) thereof. For example, when a card is used as a recording medium, it is preferable to record said parameter(s) since a card generally has a small capacity. On the other hand, when a recording medium of a large capacity, such as a floppy disk or a tape, is to be used, it is preferable to record a calibration curve itself therein.

More particularly, said calibration curve may be approximated by a general function $Y=f(X)$ wherein $Y$ represents the concentration of a substance while $X$ represents a change in the turbidity. In the above function, $f(X)$ is equal to, for example, $a_1X^n + a_2X^{n-1} \ldots a_{n+1}$; $a_1' \log X$; or $e^{a_1'' X}$.

Generally speaking, parameter(s), i.e., constant term(s) approximate to the relationship between the concentration of the substance and the change in the turbidity determined in the preparation of the reagent are determined by the method of least squares. The aimed calibration curve may be determined by substituting the parameter(s) to the above function. The parameter(s) and the form of the function, for example, $a_1X^n \ldots a_{n+1}$; $a_1' \log X$; or $e^{a_1'' X}$ are recorded in a recording medium.

When the above parameter(s) are recorded in a recording medium, a calibration curve should be formed with the use of the same before or after assaying a sample of an unknown concentration.

A sample of an unknown concentration would show a change in the turbidity when reacted with a reagent. Thus the concentration of the substance in said sample can be calculated by measuring the turbidity change and using the above-mentioned calibration curve. It is generally preferable to input a program by which the concentration of the substance can be calculated by inputting the above calibration curve as well as the turbidity or a change therein to a computer. It is unnecessary to particularly device this program but a conventional one used in the art may be employed as such therefor.

As the reagent to be used in the present invention, those stable for a prolonged period of time should be selected or prepared. For example, a reagent for turbidimetry, which comprises 3 to 33% of an antiserum, 0.9% of NaCl and 1 to 4% of polyethylene glycol 6,000 and is stable for a prolonged period of time, may be employed. Alternately a latex reagent which comprises an antigen or an antibody immobilized on latex particles; has the average reagent particle diameter (D) of 0.1 to 0.5 μm, a D to d ratio, wherein d represents the average particle diameter of latex particles, of 1.3 to 3.0, a zeta potential of −20 to 10 mV, and an absorbance at an optical path length of 10 mm of 0.5 to 1.5; and is stable for a prolonged period of time, may be employed. There have been known various latex particles available in antigen/antibody reactions. In the present invention, these latex particles can be utilized without any restriction. Particularly preferable examples thereof include organic polymer latex particles obtained through emulsion polymerization, such as polystyrene, styrene/butadiene copolymer, styrene/methacrylate copolymer, polymethyl methacrylate, polyglycidyl methacrylate and acrolein/ethylene glycol dimethacrylate copolymer; and inorganic oxides such as silica, silica/alumina or alumina, and inorganic particles obtained by introducing functional group(s) to said inorganic oxide(s) by, for example, silane coupling.

The antibody or antigen to be used in the present invention are not strictly limited but any known one may be employed. Preferable examples thereof include denatured γ-globulin, antinuclear factor, human albumin, antihuman albumin antibody, immunoglobulin G (IgG), antihuman IgG antibody, immunoglobulin A (IgA), antihuman IgA antibody, immunoglobulin M (IgM), antihuman IgM antibody, antihuman IgE antibody, streptolysin O, streptokinase, hyaluronidase, C-reactive protein (CRP), antihuman CRP antibody, α-fetoprotein (AFP), antiAFP antibody, carcinoembryonic antigen (CEA), antihuman CEA antibody, human chorionic gonadotropin (HCG), antiHCG antibody, antiestrogen antibody, antiinsulin antibody, hepatitis B surface antigen ($HB_S$), $antiHB_S$ antibody, Treponema pallidum antigen, rubella antigen, influenza antigen, complement $C_{lq}$, $antiC_{lq}$ antibody, $antiC_3$ antibody, $antiC_4$ antibody and antitransferin antibody.

In the present invention, an instrument for the determination of the turbidity or a change therein caused by an antigen/antibody complex accompanying an antigen/antibody reaction is not strictly limited but any known one may be utilized. It is generally appropriate to use a spectrophotometer, a light scattering photometer or a turbidimeter. A spectrophotometer is preferable in particular for the determination of a decrease in transmitted light. Generally speaking, when transmitted light is to be determined, any photometric apparatus which is capable of selecting a specific wavelength, provided with a mixing part by which a reagent is mixed with a sample, and can maintain a cell and the reagent at a predetermined temperature and continuously monitor a change in a signal for transmitted light caused by an antigen/antibody reaction after receiving a signal for the addition of the sample may be used. It is preferable that said apparatus is further provided with a circuit capable of outputting primary and secondary differential signals derived from said signal change.

BRIEF DESCRIPTION OF DRAWING

Figure 1:
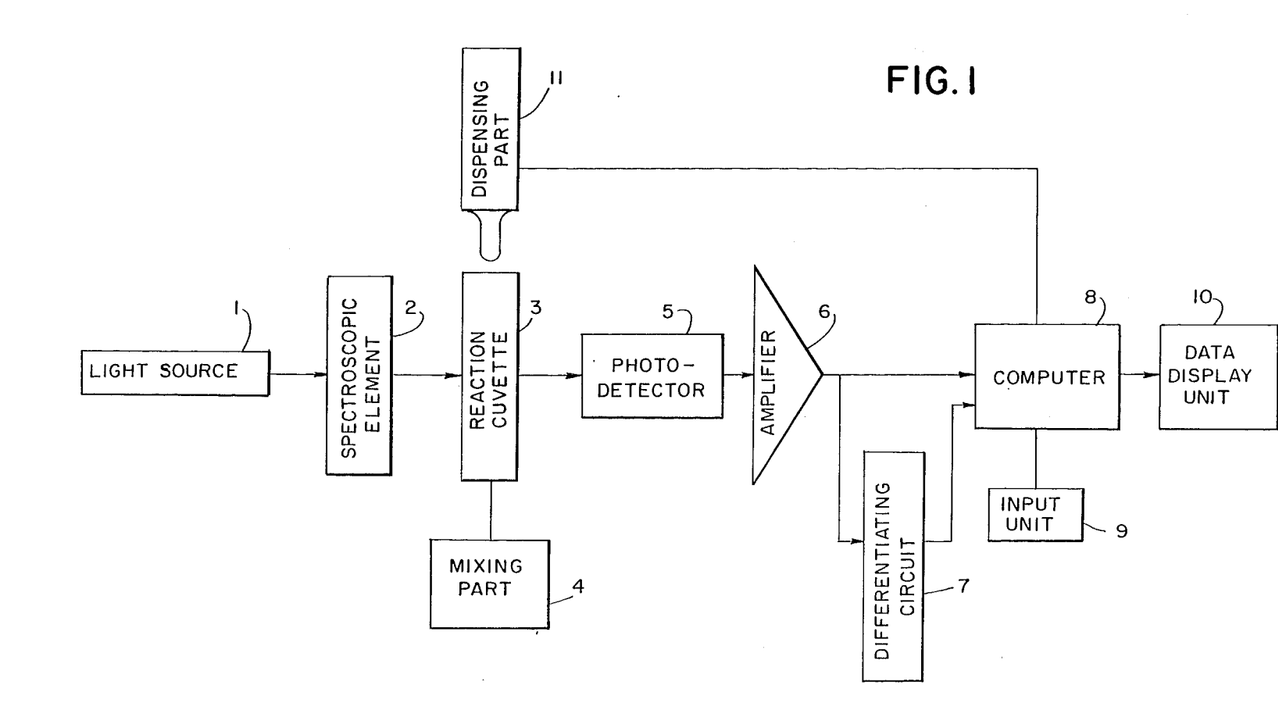

FIG. 1 is a block diagram of a system for the embodiment of the method of the present invention. In FIG. 1, light flux from a light source 1 is first led into a spectroscopic element 2 wherein light of a specific wavelength is selected. Then the selected light is led into a reaction cuvette (a photometric cell) 3 in which a reaction reagent has been preliminarily incorporated. The light transmitted through the reaction cuvette 3 is received by a photodetector 5 and converted into an electrical signal thereby. This electrical signal based on the transmitted light is amplified by an amplifier 6. One portion of the amplified electrical signal is then directly processed with a computer 8 and the concentration of the aimed antigen or antibody is thus calculated and displayed on a data display unit 10, while the other portion of the signal is parallelly subjected to a differential operation by a differentiating circuit 7. Thus the velocity of changes in the quantity of transmitted light (dA/dt) is determined and processed with the computer 8. Then the concentration of the antigen or antibody is calculated and displayed on the data display unit 10.

The system for the embodiment of the method of the present invention further comprises an input unit 9 for inputting information required for the formation of a calibration curve, a mixing part 4 for the reaction cuvette 3 and a sample dispensing part 11.

As the light source 1, a conventional one such as a tungsten lamp may be employed. The reaction cuvette 3 may be, for example, a transparent cuvette of 5 mm in internal diameter made of glass or a synthetic resin such as polystyrene.

As the spectroscopic element 2, a conventional interference filter may be used. The wavelength to be selected in the method of the present invention may be defined depending on the type of the antigen/antibody reaction. The photodetector 5 may be a conventional photocell. Examples of the input unit 9 for inputting information required for the formation of a calibration curve include a magnetic card reader, a casette tape recorder, a disk drive unit or a bar code reader.

The immunological assay method of the present invention is particularly suitable for an assay with the use of a monotest reagent as will be described below.

More precisely, a monotest reagent comprises a dispensed portion for one sample each placed in a substantially light-transmitting transparent or translucent container made of a plastic material such as polystyrene, polymethyl methacrylate, polyvinyl chloride or polypropyrene, or glass. This container also serves as a test tube as well as a cell for optical measurement. Thus a user need not prepare any additional test tubes or cells. Further, since the reagent has been already dispensed, no pipet is required. Furthermore, the containers are disposable, which makes washing of test tubes or cells unnecessary. In addition, the reagent is filled under strictly controlled conditions, which may bring about reliable results of a small error in dispensing and a high reproducibility. With the use of such a monotest reagent as described above, emergently deposited samples can be assayed merely by preparing the required portions of the reagent and a misuse of reagents would hardly occur in this case.

As described above, a monotest reagent is highly suitable for assaying a small number of samples. When an assay is to be effected with the use of a monotest reagent, in a conventional manner, however, a user should measure several standard materials for the formation of a calibration curve on each assay day. The measurement of standard materials on each assay day is not a serious problem in a large laboratory where a number of samples are treated in a day. However it is a severe burden when only several samples are to be assayed in a day. Thus the advantages of the utilization of a monotest reagent cannot be fully achieved in the latter case.

In contrast thereto, the method of the present invention makes it unnecessary to measure standard materials for the formation of a calibration curve each time for repeatedly assaying samples within the term of validity of the reagent, for example, six months. Thus the advantages of the utilization of a monotest reagent can be fully achieved.

An immunological assay kit of the present invention comprises a reagent, preferably a monotest reagent, as described above optionally combined with a recording medium selected from among the above-mentioned cards, tapes and floppy disks, in which a calibration curve or parameter(s) therefor determined in the preparation of said reagent are recorded.

Now the immunological assay method of the present invention will be systematically described.

First comes a part for forming a calibration curve or determining parameter(s) therefor based on a signal for a decrease in transmitted light or an increase in scattered light, which is caused by a change in the turbidity brought about by the formation of an antigen/antibody complex accompanying an antigen/antibody reaction, determined after a definite time or the maximum velocity or the maximum acceleration. In this calibration curve determining part, a function $Y=f(X)$, wherein Y represents the concentration of a substance to be assayed while X represents a change in the turbidity accompanying an antigen/antibody reaction, is determined based on a standard sample containing the substance to be assayed at a known concentration, as descrbbed above or as will be described in the Examples hereinafter. The parameter(s) for the function f(X) are simultaneously determined generally by the method of least squares. The above part is the most important one since the calibration curve formed therein or the parameter(s) determined therein serve as the sole data for calculating the concentrations of the substance to be assayed in samples.

The calibration curve thus formed or the parameter(s) thus determined are recorded in a recording medium, stored and optionally transmitted, for example, from a reagent manufacturer to a user. From the viewpoint of the convenience in the storage and transmission, it is preferable to use the above-mentioned cards, tapes or floppy disks as the recording medium.

The information for the calibration curve or parameter(s) therefor recorded in the recording medium are then fed to a computer provided in an analyzer and inputted to an arithmetic unit. When said information is in the form of the parameter(s), it is required to form a calibration curve therefrom. Therefore when the parameter(s) are inputted to the recording medium, it is preferable to preliminarily or simultaneously input a function for simultaneously or separately forming a calibration curve to the computer, to thereby allow the computer to form the calibration curve. In the arithmetic unit, the concentration of the substance to be assayed in a sample is calculated according to the calibration curve, which is formed depending on the turbidity or a change therein informed from the measurement part wherein the turbidity or a change therein of the substance to be assayed in the sample caused by the antigen/antibody reaction, and outputted. The program for the calculation of the outputted items from the inputted information in the arithmetic unit is not strictly limited but those conventionally used in, for example, an autoanalyzer in the art or known ones, optionally modified if required, may be used.

The essential information to be inputted in the above arithmetic unit includes the turbidity or a change therein caused by the antigen/antibody reaction between the substance to be assayed in the sample and the reagent. This information may be obtained from the sample measuring part as shown in FIG. 1. As described above, operations in this sample measuring part generally comprise detecting the turbidity or a change therein caused by the antigen/antibody reaction between the substance to be assayed in the sample and the reagent with a photodetector.

As illustrated above, the present invention provides a highly valuable immunological assay system which comprises a calibration curve determining part, a recording part, a sample measuring part and an arithmetic unit which are functionally connected to each other.

To further illustrate the present invention, and not by way of limitation, the following Examples will be given.

EXAMPLES

Example 1

(1) Reagent

A 10-mM phosphate buffer solution (pH 7.2) containing 32% of antihuman IgG antiserum (goat), 1.8% of polyethylene glycol 6,000 and 0.9% of NaCl was prepared.

(2) Formation of calibration curve

10 μl of an IgG solution of a known concentration was reacted with 650 μl of the reagent as prepared in (1) in a plastic photometric cell at 37° C. The absorbance of the reaction mixture at 450 nm was continuously measured with a nephelometer and the maximum of the primary differential values was determined.

| IgG conc. (mg/dl) | mV | IgG conc. | mV |
| --- | --- | --- | --- |
| 204 | 24.5 | 1428 | 185 |
| 408 | 54.5 | 1632 | 198 |
| 612 | 98 | 2448 | 242 |
| 816 | 116 | 2652 | 260 |
| 1020 | 137 | 2856 | 266 |
| 1224 | 16.5 | 3063 | 274 |

Based on these results, the IgG concentration was represented by Y while the primary differential value was re presented by X. When the relationship between X and Y was approximated to the following equation:

$$Y = a_1 X^4 + a_2 X^3 + a_3 X^2 + a_4 X + a_5$$

The coefficients in the above equation were determined as follows by the method of least squares:

$a_1 = -2.93 \times 10^{-7}$;
$a_2 = 2.89 \times 10^{-4}$;
$a_3 = -0.05$;
$a_4 = 9.20$; and
$a_5 = 2.06$.

These parameters $a_1$ to $a_5$ thus determined were recorded in a magnetic card with the use of a magnetic card recorder.

(3) Determination of the concentration of the substance in an unknown sample

The parameters $a_1$ to $a_5$ were inputted from the magnetic card as described above to a computer connected to the nephelometer as used in (2) with a magnetic card reader. Thus a program for calculating the equation $Y = a_1 X^4 + a_2 X^3 + a_3 X^2 + a_4 X + a_5$ was completed. Subsequently a sample of an unknown concentration was subjected to the same measurement as the one described in (2). The signal (x) thus obtained were inputted to the above computer to thereby calculate the concentration of the substance. The results are as follows:

| Time (months) | Concentration (mg/dl) |
|---|---|
| 0 | 1720 |
| 1 | 1728 |
| 2 | 1722 |
| 3 | 1726 |
| 4 | 1720 |
| 6 | 1731 |

These results suggest that the concentration determined at the starting month may be considered substantially the same as that determined after six months. Thus it has been provided that the calibration curve formed in the preparation of the reagent can give sufficiently reliable data.

Example 2

(1) Reagent

A 10-mM phosphate buffer solution (pH 7.2) containing 20% of antihuman IgA antiserum (goat), 2% of polyethylene glycol 20,000 and 0.9% of NaCl was prepared. A 400-$\mu$l portion of the solution thus obtained was dispensed into a polystyrene photometric cell of 7 mm in optical path length provided with a cylindrical stirrer and sealed with aluminum foil to which an adhesive was applied. Thus a monotest reagent was obtained.

(2) Formation of calibration curve

10 $\mu$l of an IgA solution of a known concentration was reacted with the above monotest reagent in the optical measurement part as shown in FIG. 1 under stirring at 37° C. The absorbance of the reaction mixture at 450 nm was continuously measured and the maximum of the primary differential values was determined.

| IgA conc. (mg/dl) | mV | IgA conc. (mg/dl) | mV |
|---|---|---|---|
| 42.2 | 18.8 | 302.4 | 248.0 |
| 86.4 | 83.6 | 345.6 | 275.4 |
| 129.6 | 129.0 | 388.8 | 316.6 |
| 172.8 | 165.0 | 432.0 | 344.2 |
| 216.0 | 206.3 | 475.2 | 371.1 |
| 259.2 | 238.7 | 518.4 | 406.6 |

Based on these results, the IgA concentration was represented by Y while the primary differential value was represented by X. When the relationship between X and Y was approximated to the following equation:

$$Y = a_1 X^4 + a_2 X^3 + a_3 X^2 + a_4 X + a_5$$

The coefficients in the above equation were determined as follows by the method of least squares:

$a_1 = -1.69 \times 10^{-2}$;
$a_2 = -1.98 \times 10^{-8}$;
$a_3 = 7.85 \times 10^{-5}$;
$a_4 = 1.24 \times 10^{-2}$; and
$a_5 = 19.2$.

This equation, i.e., $Y = a_1 X^4 + a_2 X^3 + a_3 X^2 + a_4 X = a_5$ was recorded in a floppy disk with the use of a disk drive unit.

(3) Determination of the concentration of the substance in an unknown sample

A calibration curve corresponding to the equation $Y = a_1 X^4 + a_2 X^3 + a_2 X^2 + a_4 X + a_5$ was read from said floppy disk with a built-in disk drive unit provided in a computer connected to the nephelometer as used in (2). Then a sample of an unknown concentration was subjected to the same measurement as the one described in (2). The signals X thus obtained were inputted of the computer. Thus the concentrations of the substance was calculated as follows:

| Time (months) | Conc. (mg/dl) |
|---|---|
| 0 | 221 |
| 1 | 224 |
| 2 | 227 |
| 3 | 222 |
| 4 | 230 |
| 6 | 220 |

These results suggest that the concentration determined at the starting month may be considered substantially the same as that determined after six months. Thus it has been proved that the calibration curve formed in the preparation of the reagent can give sufficiently reliable data.

Example 3

(1) Reagent

A 10-mM phosphate buffer solution (pH 7.2) containing 8% of antihuman IgM antiserum (goat), 2.3% of polyethylene glycol 20,000 and 0.9% of NaCl was prepared.

(2) Formation of calibration curve

20 $\mu$l of an IgM solution of a known concentration was reacted with 400 $\mu$l of the reagent as prepared in (1) in a plastic photometric cell at 37° C. The absorbance of the reaction mixture at 450 nm was continuously measured with a nephelometer and the maximum of the primary differential values was determined.

| IgM conc. (mg/dl) | mV | IgM conc. (mg/dl) | mV |
|---|---|---|---|
| 26.2 | 7.7 | 157.2 | 63.3 |
| 52.4 | 15.8 | 183.4 | 71.7 |
| 78.6 | 26.4 | 209.6 | 81.8 |
| 104.8 | 38.4 | 235.8 | 91.2 |
| 131.0 | 50.3 | 262.0 | 108.6 |

Based on these results, the IgM concentration was represented by Y while the primary differential value was represented by X. When the relationship between X and Y was approximated to the following equation:

$$Y = a_1 X^4 + a_2 X^3 + a_3 X^2 + a_4 X + a_5$$

The coefficients in the above equation were determined as follows by the method of least squares:

$a_1 = -4.88 \times 10^{-10}$;
$a_2 = 1.08 \times 10^{-6}$;
$a_3 = -7.81 \times 10^{-4}$;
$a_4 = 0.441$; and
$a_5 = -1.35$.

These parameters $a_1$ to $a_5$ were recorded in a cassette tape with the use of a cassette tape recorder.

(3) Determination of the concentration of the substance in an unknown sample

The parameters $a_1$ to $a_5$ were inputted from said cassette tape to a computer connected to the nephelometer as used in (2) with a cassette tape reader and a program fro calculating the equation $$Y = a_1 X^4 + a_2 X^3 = a_3 X^2 + a_4 X + a_5$$

was completed. Then a sample of an unknown concentration was subjected to the same measurement as the one described in (2) and the concentration was calculated from the signals X thus obtained by using the computer. The results are as follows:

| Time (months) | Conc. (mg/dl) |
| --- | --- |
| 0 | 132 |
| 1 | 130 |
| 2 | 129 |
| 3 | 132 |
| 4 | 130 |
| 6 | 135 |

These results suggest that the concentration determined at the starting month may be considered substantially the same as that determined after six months. Thus it has been proved that the calibration curve formed in the preparation of the reagent can give sufficiently reliable data.

Example 4

(1) Reagent

A 10-mM phosphate buffer solution (pH 7.2) containing 15% of antihuman $C_3$ antiserum (goat), 1.7% of polyethylene glycol 20,000 and 0.9% of NaCl was prepared. (2) Formation of calibration curve 20 μl of a $C_3$ solution of a known concentration was reacted with 400 μl of the reagent as prepared in (1) in a plastic photometric cell at 37° C. The absorbance of the reaction mixture at 450 nm was continuously measured with a nephelometer and the maximum of the primary differential values were determined.

| $C_3$ conc. (mg/dl) | mV | $C_3$ conc. (mg/dl) | mV |
| --- | --- | --- | --- |
| 17.1 | 18.0 | 170.5 | 196.5 |
| 34.1 | 45.2 | 204.6 | 241.2 |
| 68.2 | 95.3 | 238.7 | 280.7 |
| 102.3 | 130.4 | 272.8 | 281.3 |
| 136.4 | 172.9 | 306.9 | 316 |

Based on these results, the $C_3$ concentration was represented by Y while the primary differential value was represented by X. When the relationship between X and Y was approximated to the following equation:

$$Y = a_1 X^4 + a_2 X^3 + a_3 X^2 + a_4 X + a_5$$

The coefficients in the above equation were determined as follows by the method of least squares:

$a_1 = 3.00 \times 10^{-12}$;
$a_2 = -1.59 \times 10^{-8}$;
$a_3 = 3.84 \times 10^{-5}$;
$a_4 = 5.13 \times 19^{-2}$; and
$a_5 = 3.11$ These parameters $a_1$ to $a_5$ were recorded in a magnetic card with a magnetic card recorder.
(3) Determination of the concentration of the substance in an unknown sample The parameters $a_1$ to $a_5$ were inputted from said magnetic card to a computer connected to the nephelometer as used in (2) with a magnetic card recorder. Thus a program for calculating the equation $Y = a_1 X^4 + a_2 X^3 + a_3 X^2 + a_4 X + a_5$ was completed. A sample of an unknown concentration was subjected to the same measurement as the one described in (2) and the concentration of the substance was calculated from the obtained signals X with the computer. The results are as follows:

| Time (months) | Conc. (mg/dl) |
| --- | --- |
| 0 | 103 |
| 1 | 100 |
| 2 | 102 |
| 3 | 99 |
| 4 | 101 |
| 6 | 104 |

These results suggest that the concentration determined at the starting month may be considered substantially the same as that determined after six months. Thus it has been proved that the calibration curve formed in the preparation of the reagent can give sufficiently reliable data.

Example 5

(1) Reagent

A 10-mM phosphate buffer solution (pH 7.2) containing 6% of antihuman $C_4$ antiserum (goat), 1.6% of polyethylene glycol 20,000 and 0.9% of NaCl was prepared.
(2) Formation of calibration curve 20 μl of a $C_4$ solution of a known concentration was reacted with 400 μl of the reagent as prepared in (1) in a glass photometric cell at 37° C. The reaction mixture was irradiated with light and the resulting scattered light was continuously measured with a nephelometer. The maximum of the primary differential values thereof was determined.

| $C_4$ conc. (mg/dl) | mV | conc. (mg/dl) | mV |
| --- | --- | --- | --- |
| 3.4 | 6.1 | 33.5 | 43.4 |
| 6.7 | 8.7 | 40.2 | 54.5 |
| 13.5 | 16.5 | 46.9 | 62.2 |
| 20.1 | 26.5 | 53.7 | 69.6 |
| 26.8 | 34.7 | 60.7 | 78.6 |

Based on these results, the $C_4$ concentration was represented by Y while the primary differential value was represented by X. When the relationship between X and Y was approximated to the following equation:

$$Y = a_1 X^4 + a_2 X^3 + a_3 X^2 + a_4 X + A_5$$

The coefficients in the above equation were determined as follows by the method of least squares:

$a_1 = -7.76 \times 10^{-11}$;
$a_2 = 1.36 \times 10^{-7}$;
$a_3 = -7.78 \times 10^{-5}$;
$a_4 = 9.17 \times 10^{-2}$; and
$a_5 = -0.707$.

These parameters $a_1$ to $a_5$ were recorded in a magnetic card with a magnetic card recorder.
(3) Determination of the concentration of the substance in an unknown sample The parameters $a_1$ to $a_5$ were inputted from said magnetic card to a built-in CPU and memory provided in the apparatus as used in (2) with a built-in magnetic card reader similarly provided therein. Thus a program for calculating the equation $Y = a_1 X^4 + a_2 X^3 + a_3 X^2 a_4 X + a_5$ was completed. A sample of an unknown concentration was subjected to the same measurement at the one described in (2) and the concentration of the substance was calculated from the obtained signals X with the comptuer. The results were as follows:

| Time (months) | Conc. (mg/dl) |
|---|---|
| 0 | 25.2 |
| 1 | 26.3 |
| 2 | 25.8 |
| 3 | 25.5 |
| 4 | 25.7 |
| 6 | 25.0 |

These results suggest that the concentration determined at the starting month may be considered substantially the same as that determined after six months. Thus it has been provided that the calibration curve formed in the preparation of the reagent can give sufficiently reliable data.

Example 6

(1) Preparation of reagent for assaying rheumatoid factor

Polystyrene latex particles of 0.178 μm in average diameter were diluted with a borate buffer solution (0.1M, pH 8.2, NaCl 0.5M), which will be abbreviated as BBS hereinafter, to give a suspension containing 1% by weight to the latex particles. Then human IgG treated at 60° C. for ten minutes was diluted with BBS to give a concentration of 1 mg/ml. To one part by volume of the above latex suspension, one part by volume of the heat aggregated human IgG solution was added under stirring at a controlled rate, while analyzing the mixture with a particle analyzer in such a manner as to give a D to d ratio of 1.3 to 3.0, wherein D was the average diameter of the latex reagent particles while d was that of the latex particles. After allowing to stand for two hours, the mixture was centrifuged and the supernatant was removed. Then the precipitate was redispersed in BBS containing 0.05% by weight of bovine serum albumin to give a latex concentration of 0.03% by weight. Thus a reagent for assaying rheumatoid factor was obtained. When analyzed with a particle analyzer, the average particle diameter of the latex reagent was 0.240 μm. The zeta potential of the reagent determined by LASER ZEE Model 501 (mfd. by PEN KEN Inc.) was $-2.5\pm0.2$ mV (in BBS). The absorbance of the latex reagent at 580 nm was 1.25 (optical path length: 10 mm).

(2) Assay method

The absorbance was measured with an autographic spectrometer U-3200 (mfd. by Hitachi, Ltd.) provided with a temperature control unit and a magnetic stirrer at the measurement part. A cylindrical stirrer was introduced into a glass photometric cell of 10 mm in optical path length. Then 1980 μl of the reagent for assaying rheumatoid factor as prepared in (1) was dispensed thereto and the cell was inserted into the measurement part of the spectrophotometer, wherein it was kept at 37° C.

Subsequently the reagent for assaying rheumatoid factor was stirred with the stirrer while 20 μl of a sample solution was added thereto. The determination of the absorbance was initiated simultaneously with the addition. The absorbance was determined by using light of 580 nm in wavelength. The stirring was ceased three seconds after the addition of the sample solution.

(3) ormation of calibration curve

Sample rheumatoid factor solutions of concentrations of 5, 10, 20, 40, 80, 100, 200, 500 and 1000 IU/ml were prepared by diluting a pool serum containing 1600 IU/ml of rheumatoid factor obtained from rheumatoid patients with a physiological saline. The absorbances of these nine sample solutions and BBS were determined each five times under the same conditions as those defined in (2).

The difference in the absorbance between the solution determined after one minute and the one after five minutes was calculated. Table 1 shows the results.

TABLE 1

| R. factor conc. in sample (IU/ml) | Difference in absorbances after definite period*[1] | | |
|---|---|---|---|
| | Average | Standard deviation | Coefficient of variation |
| 0*[2] | 0.0003 | 0.0006 | 200 (%) |
| 5 | 0.0163 | 0.0013 | 8.2 |
| 10 | 0.0382 | 0.0019 | 5.0 |
| 20 | 0.0764 | 0.0025 | 3.3 |
| 40 | 0.1751 | 0.0037 | 2.1 |
| 80 | 0.3511 | 0.0063 | 1.8 |
| 100 | 0.4135 | 0.0029 | 0.7 |
| 200 | 0.4021 | 0.0024 | 0.6 |
| 500 | 0.3811 | 0.0030 | 0.8 |
| 1000 | 0.3789 | 0.0030 | 0.8 |

*[1]The average and standard deviations are obtained by measuring each sample five times. The coefficient of variation is determined by dividing the standard deviation by the average.
*[2]BBS was employed as a sample solution.

The results as shown in Table 1 were closely approximate to the following equation (1) seven days after the preparation of the reagent:

$$Y = (42.95X + 1.047) \times 1/1000 \qquad (1)$$

wherein the ordinate(Y) refers to the average difference in the absorbance, while the abscissa(X) refers to the concentration of rheumatoid factor in the sample.

The parameters in the equation (1), i.e., $A = 42.95 \times 1/1000$ and $B = 1.047 \times 1/1000$ were recorded in a magnetic card with a magnetic card recorder.

(4) Assay of unknown sample

The parameters A and B were inputted from the magnetic card to a computer with a magnetic card reader connected to the comptuer and a program for calculating the equation $Y = (42.95X + 1.047) \times 1000$ was completed.

A serum sample containing rheumatoid factor at an unknown concentration was assayed in the same manner as the one described in (2). According to the calibration curve of the equation (1), the concentration of rheumatoid factor therein determined seven days after the preparation of the reagent was 59.0 IU/ml. The same reagent was stored at 4° C. for 12 months and then the same assay was carried out again. The concentration thus calculated with the computer according to the calibration curve of the equation (1) was 56.9 IU/ml.

Thus it has been proved that an accurate assay can be effected after 12 months with the use of the calibration curve formed in the preparation of the reagent (seven days thereafter).

The reagent stored at 4° C. for 12 months had an average particle diameter of 0.24 μm, a zeta potential of $-2.3\pm0.2$ mV and an absorbance of 1.26.

Example 7

(1) Preparation of reagent for assaying C-reactive protein (CRP)

Polystyrene latex particles of 0.123 μm in average diameter were diluted with an ammonium chloride/ammonia buffer solution (pH 8.0) to give a suspension containing 1% by weight of the latex particles. Then an antiCRP goat IgG fraction, which was obtained by salting out antiCRP serum obtained by immunizing a goat with CRP, was diluted with an ammonium chloride/ammonia buffer solution (pH 8.0) to give a solution containing 2 mg/ml of the protein. To one part by volume of the above latex suspension, one part by volume of the antiCRP goat IgG solution was added under stirring at a controlled rate similar to Example 6 and the resulting mixture was allowed to react at 37° C. for two hours. Then the obtained reaction mixture was centrifuged and the supernatant was removed. The precipitate was redispersed into an ammonium chloride/ammonia buffer solution (pH 8.0) containing 0.05% by weight of bovine serum albumin to thereby adjust the latex concentration to 0.05% by weight. Thus a reagent for assaying CRP was obtained.

When analyzed with a particle analyzer, the average particle diameter of the latex reagent was 0.213 μm. The surface charge density thereof in an ammonium chloride/ammonia buffer solution was $-2.0 \pm 0.2$ mV while the absorbance thereof was 1.30.

(2) Assay method

The procedure of Example 6 was followed except that 1990 μl of the reagent and 10 μl of a sample solution were employed.

(3) Formation of calibration curve

Samples containing 0.10, 0.25, 0.50, 1.0, 2.5, 5.0, 10, 15, 20, 30, 40 and 60 mg/dl of CRP were prepared by diluting a purified CRP solution containing 240 mg/dl of CRP with CRP-free serum obtained by substantially removing CRP through absorption.

The absorbances of these 12 samples solutions and an ammonium chloride/ammonia buffer solution were determined each five times under the same conditions as employed in (2).

The difference in the absorbance between the sample determined after one minute and the one after five minutes was calculated. When the average difference in the absorbance was referred to X while the CRP concentration in the sample was referred to Y, these data were closely approximated to the following equation at a level of 10 mg/dl or below:

$$Y = exp(1.011 \ln X + 3.204) \quad (2)$$

A calibration curve according to the equation (2) was inputted in a floppy disk. (4) Assay of unknown sample The floppy disk in which the equation (2) was inputted to a computer and a program for calculating the CRP concentration of an unknown sample according thereto was completed.

A serum sample of an unknown CRP concentration was assayed with the elapse of time in the same manner as the one described in (2). The absorbance X thus obtained was inputted to the calibration curve of the equation (2) as formed in the preparation of the reagent and the concentration of the sample was calculated with the computer. The result was as follows:

| Time after the preparation of reagent | Conc. (mg/dl) |
|---|---|
| 7 days | 4.3 |
| 3 months | 4.3 |
| 6 months | 4.1 |
| 9 months | 4.1 |
| 12 months | 4.0 |

Thus it has been proved that an accurate assay can be effected after 12 months by using the calibration curve formed in the preparation of the reagent (seven days thereafter). The reagent was stored at 4° C.

The reagent stored at 4° C. for 12 months had an average particle diamete of 0.214 μm, a surface charge density of $-2.1 \pm 0.3$ mV and an absorbance of 1.31.

Example 8

(1) Preparation of reagent for assaying rheumatoid factor

A 1980-μl portion of the reagent as prepared in Example 6 was dispensed in a polystyrene cuvette provided with a cylindrical stirrer and having an optical path length of 10 mm and sealed with aluminum foil to which an adhesive was applied. Thus a monotest reagent was obtained.

(2) Assay method

An assay was effected with an apparatus having the function as shown in the block diagram (FIG. 1). The monotest reagent for assaying rheumatoid factor (3) was inserted into an optical measurement part and heated to 37° C. Then the reagent was stirred with a stirrer (4) while 20 μl of a sample was dispensed thereto through a sample dispensing unit 11. The determination of the absorbance of the mixture was initiated simultaneously with the addition. The absorbance was determined by selecting light of 580 nm in wavelength from white light from a tungsten lamp (1) with a spectroscopic element (2). The stirring was ceased three seconds after the addition of the sample.

(3) Formation of calibration curve

A calibration curve was formed in the same manner as the one described in Example 6–(3). The resulting calibraiton curve was closely approximated to the following equation:

$$Y = (44.27X + 1.081) \times 1/1000 \quad (3)$$

wherein Y represents the average difference in the absorbance while X represents the concentration of rheumatoid factor therein.

The parameters in the equation (3), i.e., $A = 44.27 \times 1/1000$ and $B = 1.081 \times 1/1000$ were recorded in a magnetic card with a magnetic card recorder.

(4) Assay of unknown sample

The magnetic card in which the parameters for the calibration curve were inputted was inputted to a computer (8) via an inputting unit (9) and a program for calculating the equation $Y = (44.27X + 1.081) \times 1/1000$ was completed.

A serum sample of an unknown rheumatoid factor concentration was assayed with the elapse of time in the same manner as the one described in (2) according to the calibration curve as formed in the preparation of the reagent. As a result, the following concentrations were displayed on a data display unit (10).

| Time after the preparation of reagent | Conc. (IU/ml) |
| --- | --- |
| 0 | 59.0 |
| 3 months | 59.2 |
| 6 months | 58.9 |
| 9 months | 57.3 |
| 12 months | 57.7 |

Thus it has been proved that a sufficiently reliable assay can be effected with the use of the calibration curve as formed in the preparation of the onetest reagent. The reagent was stored at 4° C.

Example 9 (1) Preparation of reagent for assaying antistreptolysin O antibody (ASO)

Polystyrene latex particles of 0.123 μm in average particle diameter were diluted with a borate buffer solution (0.1M, pH 8.2, NaCl 0.5M), which will be abbreviated as BBS hereinafter, to give a suspension containing 1% by weight of the latex particles. A culture supernatant of β-hemolytic streptrococcus was fractionated and purified in a conventional manner to give streptolysin O (SLO). The hemolytic activity of the obtained SLO was 12,000 U/ml. Then the SLO solution was diluted ten-fold with BBS. To one part by volume of the above latex suspension, one part by volume of the SLO solution was added under stirring at a controlled rate in such a manner as to give a D to d ratio of 1.3 to 3.0, wherein D represents the average particle diameter of the latex reagent while d represents the average particle diameter of the latex particles, similar to Example 6. The resulting mixture was allowed to react at 37° C. for two hours, followed by heating to 45° C. for 30 minutes under stirring. Then it was centrifuged and the supernatant was removed. The precipitate was redispersed in BBS containing 0.05% by weight of bovine serum albumin to give a latex concentration of 0.05% by weight. Thus an ASO reagent was obtained.

When analyzed with a particle analyzer, the latex reagent had an average particle diameter of 0.257 μm. The surface charge density thereof was $-1.5\pm0.1$ mV (in BBS) while the absorbance thereof at 580 nm was 1.42 (optical path length: 10 mm).

A 990-μl portion of this ASO reagent was dispensed into a glass cuvette provided with cylindrical stirrer and having an optical path length of 10 mm and sealed with a parafilm to thereby prevent leakage of moisture and the solution. Thus a monotest reagent was obtained.

(2) Assay method

An assay was carried out with an apparatus having the functions as shown in the block diagram (FIG. 1). The ASO monotest reagent (3) was inserted into an optical measurement part and heated to 37° C. Then 10 μl of a sample was added to the reagent via a sample dispensing unit (11) while stirring the reagent with a stirrer (4). The determination of the turbidity was initiated simultaneously with the addition. The turbidity was determined by using light from a tungsten lamp (1) without using a spectroscopic element (2). The stirring was ceased five seconds after the addition of the sample. The turbidity was determined as the ratio of the scattered light intensity to the transmitted light intensity with the use of an integrated spherical turbidimeter SEP PT-501 D (mfd. by Nippon Seimitsu Kogaku Co., Ltd.).

(3) Formation of calibration curve

The serum of a patient infected with hemolytic streptococcus containing 4,000 IU/ml of ASO was diluted with a physiological saline to give samples of ASO concentrations of 10, 40, 160, 640, 1280 and 2560 IU/ml. The turbidities of these six samples and BBS were determined under the same conditions as those employed in (2) each five times.

The calibration curve thus obtained was closely approximated to the following equation:

$$Y = 6.25 \times 10^{-4} X + 0.215 \quad (4)$$

wherein Y represents the average change in the turbidities determined one minute and give minutes after the addition of each sample while X represents the ASO concentration of the sample. These parameters for the equation (4), i.e., $A = 6.25 \times 10^{-4}$, $B = 0.215$) were recorded in a magnetic card with a magnetic card recorder.

(4) Assay of unknown sample

The magnetic card, in which the parameters for the calibration curve were recorded, was inputted to a computer (8) with an inputting unit (9) and a program for calculating an equation $Y = 6.25 \times 10 X + 0.215$ was completed.

A serum sample of an unknown ASO concentration was assayed with the elapse of time in the same manner as the one described in (2) according to the calibration curve as formed in the preparation of the reagent. Thus the following concentrations were obtained:

| Time after the preparation of reagent | ASO conc. (IU/ml) |
| --- | --- |
| 0 | 337.1 |
| 6 months | 329.8 |
| 12 months | 327.1 |

Thus it has been found that a sufficiently reliable assay can be effected with the use of the monotest reagent according to the calibration curve as formed in the preparation of the reagent. The reagent was stored at 6° C.

The reagent stored at 6° C. for 12 months had an average particle diameter of 0.259 μm, a surface charge density of $-1.7\pm0.2$ mV and an absorbance of 1.46.

What is claimed is:

1. An immunological assay for an analyte in a sample wherein calibration curves for assay results are prepared based on a change in transmitted or scattered light caused by a change in turbidity accompanying formation of an antigen-antibody complex by an antigen-antibody reaction comprising:

providing a latex particle containing reagent having an average reagent particle diameter (D) in the range of 0.1 to 0.5 μm, a D to d ratio (D/d), wherein d represents the average particle diameter of said latex particles, in the range of 1.3 to 3.0 and a zeta potential in the range of $-20$ to 10 mV, for use in said assay;

obtaining calibration curves or parameters which make up calibration curves for said latex particle containing reagent used in the assay;

providing said calibration curves or said parameters in a magnetic medium;

outputting said calibration curves or calibration curves that have been prepared using of said parameters from said magnetic medium to an analyzer;

said analyzer being incorporated into a computer;

reacting in said analyzer said latex particle containing reagent with a sample;

obtaining any change in transmitted or scattered light caused by any change inturbidity accompanying any formation of an antigen-antibody complex by an antigen-antibody reaction;

and comparing any change in transmitted or scattered light with said calibration curves for said latex particle containing reagent in order to determine the amount of analyte in said sample.

2. The method according to claim 1, wherein said magnetic medium is selected from the group consisting of magnetic tapes, magnetic cards, and floppy disks.

* * * * *

UNITED STATES PATENT AND TRADEMARK OFFICE
CERTIFICATE OF CORRECTION

PATENT NO. : 4,843,021
DATED : June 27, 1989
INVENTOR(S) : NOGUCHI et al.

It is certified that error appears in the above-identified patent and that said Letters Patent is hereby corrected as shown below:

Column 5, line 36    Delete "antitransferin", insert therefor -- antitransferrin --

Column 16, line 12    Before "reagent", insert --monotest--

Signed and Sealed this

Thirty-first Day of December, 1991

Attest:

HARRY F. MANBECK, JR.

*Attesting Officer*    *Commissioner of Patents and Trademarks*